(12) United States Patent
Atkinson et al.

(10) Patent No.: US 9,694,098 B2
(45) Date of Patent: *Jul. 4, 2017

(54) REMOTELY DEPLOYABLE VAPOR DELIVERY DEVICE

(71) Applicant: SimpleTek LLC, Richmond, VA (US)

(72) Inventors: Gary M. Atkinson, Henrico, VA (US); Glenn Willoughby, Richmond, VA (US)

(73) Assignee: SimpleTek LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/989,099

(22) Filed: Jan. 6, 2016

(65) Prior Publication Data
US 2016/0114070 A1 Apr. 28, 2016

Related U.S. Application Data

(63) Continuation of application No. 13/232,411, filed on Sep. 14, 2011, now Pat. No. 9,259,499.
(Continued)

(51) Int. Cl.
*A24F 25/00* (2006.01)
*A61L 9/12* (2006.01)
*A01M 1/20* (2006.01)

(52) U.S. Cl.
CPC .......... *A61L 9/127* (2013.01); *A01M 1/2044* (2013.01)

(58) Field of Classification Search
CPC . A61L 9/127; A61L 9/037; A61L 9/12; A61L 9/04; A01M 1/2044; A01M 1/2055; A01M 9/127
(Continued)

(56) References Cited

U.S. PATENT DOCUMENTS 1,871,949 A 8/1932 Bottrell
3,685,734 A 8/1972 Paciorek et al.
(Continued)

OTHER PUBLICATIONS

Office Action in U.S. Appl. No. 13/232,411; dated Aug. 25, 2015; 6 pages.
(Continued)

*Primary Examiner* — Davis Hwu
(74) *Attorney, Agent, or Firm* — John H. Thomas, P.C.

(57) ABSTRACT

A remotely deployable vapor delivery device is described that is conveniently and effectively deployed in a hard-to-reach location. The device is approximately spherical in shape, and includes an integrated reservoir containing the desired vapor producing substance, an evaporative surface and means for continuous flow of the vapor producing substance from the integrated reservoir to the evaporative surface which provides an approximately constant vapor delivery rate. The advantages of the embodiments include a device that can be conveniently tossed or rolled, is compact in size, provides a maximal amount of stored vapor producing substance, has an efficient usage rate of the stored vapor producing substance and provides a long operating lifetime. Other advantages of the embodiments described include hands-free activation, self-righting after deployment, tamper resistance, non-energized operation, a modest number of low cost parts that are readily manufactured and assembled, and easy retrieval.

9 Claims, 5 Drawing Sheets

Related U.S. Application Data

(60) Provisional application No. 61/383,217, filed on Sep. 15, 2010.

(58) Field of Classification Search
USPC .................. 239/34, 40–44, 47, 51.5, 55, 57
See application file for complete search history.

(56) References Cited

U.S. PATENT DOCUMENTS

| | | | |
|---|---|---|---|
| 3,706,140 A | 12/1972 | Brillaud et al. |
| 3,790,081 A | 2/1974 | Thornton et al. |
| 4,161,283 A | 7/1979 | Hyman |
| 4,161,284 A | 7/1979 | Rattan |
| 4,286,754 A | 9/1981 | Jones |
| 4,323,193 A | 4/1982 | Compton et al. |
| 4,413,779 A | 11/1983 | Santini |
| 4,621,768 A | 11/1986 | Lhoste et al. |
| 4,647,433 A | 3/1987 | Spector |
| 4,660,763 A | 4/1987 | Gutkowski et al. |
| 4,695,434 A | 9/1987 | Spector |
| 4,739,928 A | 4/1988 | O'Neil |
| 4,889,286 A | 12/1989 | Spector |
| 4,913,350 A | 4/1990 | Purzycki |
| 4,928,881 A | 5/1990 | Barlics et al. |
| 4,948,047 A | 8/1990 | Zembrodt |
| 5,121,881 A | 6/1992 | Lembeck |
| 5,242,111 A | 9/1993 | Nakoneczny et al. |
| 5,395,047 A | 3/1995 | Pendergrass, Jr. |
| 5,735,460 A | 4/1998 | Eisenbraun |
| 5,749,519 A | 5/1998 | Miller |
| 5,749,520 A | 5/1998 | Martin et al. |
| 5,765,751 A | 6/1998 | Joshi |
| 5,865,372 A | 2/1999 | Ceresko |
| 5,875,968 A | 3/1999 | Miller et al. |
| 5,876,678 A | 3/1999 | Harrell et al. |
| 5,899,382 A | 5/1999 | Hayes et al. |
| 6,029,900 A | 2/2000 | Quinones |
| 6,104,867 A | 8/2000 | Stathakis et al. |
| 6,580,875 B2 | 6/2003 | Rymer |
| 6,581,915 B2 | 6/2003 | Bartsch et al. |
| 6,699,432 B2 | 3/2004 | Channer |
| 6,749,672 B2 | 6/2004 | Lynn |
| 6,871,794 B2 | 3/2005 | McEwen |
| 6,913,733 B2 | 7/2005 | Hardy et al. |
| 7,028,917 B2 | 4/2006 | Buthier |
| 7,111,794 B2 | 9/2006 | Timpson |
| 7,160,515 B2 | 1/2007 | Murdell et al. |
| 7,223,361 B2 | 5/2007 | Kvietok et al. |
| 7,350,720 B2 | 4/2008 | Jaworski et al. |
| 7,379,662 B2 | 5/2008 | Caserta et al. |
| 7,380,370 B2 | 6/2008 | Livingston |
| 7,431,901 B2 | 10/2008 | Stiros et al. |
| 7,597,309 B1 | 10/2009 | Stucki |
| 7,798,422 B2 | 9/2010 | Trevino |
| 7,909,264 B2 | 3/2011 | Dunne et al. |
| 9,259,499 B2 * | 2/2016 | Atkinson ............... A61L 9/127 |
| 2001/0014983 A1 | 8/2001 | Bryson, Jr. et al. |
| 2002/0066798 A1 | 6/2002 | Laudamiel-Pellet et al. |
| 2002/0068009 A1 | 6/2002 | Laudamiel-Pellet et al. |
| 2002/0068010 A1 | 6/2002 | Laudamiel-Pellet et al. |
| 2003/0012680 A1 | 1/2003 | Balsys |
| 2003/0080197 A1 | 5/2003 | Tuomikoski et al. |
| 2003/0094503 A1 | 5/2003 | Rymer et al. |
| 2003/0175148 A1 | 9/2003 | Kvietok et al. |
| 2004/0007787 A1 | 1/2004 | Kvietok et al. |
| 2004/0067172 A1 | 4/2004 | Ehrlich et al. |
| 2004/0265164 A1 | 12/2004 | Woo et al. |
| 2005/0031498 A1 | 2/2005 | Held |
| 2005/0214158 A1 | 9/2005 | Kvietok et al. |
| 2005/0265904 A1 | 12/2005 | Hardy et al. |
| 2006/0078477 A1 | 4/2006 | Althouse et al. |
| 2006/0081721 A1 | 4/2006 | Caserta et al. |
| 2006/0100303 A1 | 5/2006 | Bedford et al. |
| 2006/0226251 A1 | 10/2006 | Helf et al. |
| 2007/0001023 A1 | 1/2007 | Green et al. |
| 2007/0065332 A1 | 3/2007 | Stiros et al. |
| 2007/0290066 A1 | 12/2007 | McGee et al. |
| 2008/0035670 A1 | 2/2008 | Timmann et al. |
| 2008/0061162 A1 | 3/2008 | Zarembinski |
| 2008/0087740 A1 | 4/2008 | Gusenoff et al. |
| 2009/0162253 A1 | 6/2009 | Porchia et al. |

OTHER PUBLICATIONS

Office Action in U.S. Appl. No. 13/232,411; dated May 1, 2015; 6 pages.
Office Action in U.S. Appl. No. 13/232,411; dated Jan. 23, 2015; 5 pages.
Office Action in U.S. Appl. No. 13/232,411; dated Sep. 4, 2014; 6 pages.
Office Action in U.S. Appl. No. 13/232,411; dated Apr. 18, 2014; 6 pages.
Office Action in U.S. Appl. No. 13/232,411; dated Dec. 16, 2013; 6 pages.
Office Action in U.S. Appl. No. 13/232,411; dated Sep. 10, 2013; 14 pages.

* cited by examiner

REMOTELY DEPLOYABLE VAPOR DELIVERY DEVICE

CROSS-REFERENCE TO RELATED APPLICATIONS

This application claims the benefit of U.S. Provisional Patent Application No. 61/383,217, filed Sep. 15, 2010 and is a continuation of U.S. patent application Ser. No. 13/232,411, filed Sep. 14, 2011, which are incorporated herein by reference.

This application relates to the field of supplying an air-modifying vapor to a difficult to reach location. Specifically, the application describes a remotely deployable vapor delivery device for emitting or releasing a volatile air-modifying vapor or agent to the surrounding air of a hard to reach or inaccessible location. In general, the purposes for such vapor delivery systems can be for masking odors, providing a pleasing aroma or also to provide an aroma that is noxious or discouraging to rodents or pests for the purposes or repelling them. One example of the use of such a device is for discouraging rodents or pests from entering a house by providing a discouraging vapor at their known entry points.

BACKGROUND

In regard to natural air-modifying agents that repel vermin, there are a number of aromatic oils, such as peppermint, eucalyptus and spearmint which are well known and sold commercially for this purpose. An example is the Mouse Away line of products from Dreaming Earth Botanicals. Peppermint oil can be a key ingredient in a rodent repelling solution. The delivery method for the Mouse Away products is simply to use an absorbing medium which is impregnated with their proprietary blend of spearmint and peppermint oils. The device is placed in the desired location and the vapor evaporates from all of the exposed surfaces of the device. Additionally, simply soak a cotton ball and place it in the desired location. This simple device will function in the same manner, repelling rodents for a relatively short period of time. One disadvantage of this "Soaked Cotton Ball" approach is the non-constant delivery rate of the peppermint oil vapor from such a device. The Mouse Away products are essentially equivalent to the "soaked cotton ball" in that an absorbing material is saturated with the oil solution and simply allowed to evaporate from there.

In this basic soaked cotton ball approach, the evaporative surface will be soaked to its highest level at the start and as the material evaporates, the surface concentration will drop. The vapor delivery rate, which is proportional to surface area and concentration at that surface, will then be a maximum at the start of the operation of the device and will simply decrease with time. Since it is generally desirable to modify the air for the desired purpose both at a particular level and for the longest period of time possible, it is readily apparent that this approach accomplishes neither. Because the delivery rate decreases with time, it must be designed to be significantly higher than required at the start in order to gain an appreciable lifetime of operation. In other words, excess vapor delivery is required at the start of operation.

For the case of repelling rodents, it can be appreciated that a certain concentration of vapor is required to effectively repel them from an area. At some point the simple soaked cotton ball device dries out to the extent that the concentration of the evaporating vapor falls below an effective level and the device ceases to function as desired. In such a simple device, the only time that the device produces the minimum but effective dose is just prior to the device becoming ineffective.

Clearly, one main disadvantage of this simple soaked cotton ball approach is that the delivery rate of the vapor is not optimized. The vapor delivery rate must necessarily be at or above the required level to start, and then will continually decrease, falling below the desired level at some point in time. The maximum total lifetime of the device is attained by soaking the absorbing material until it is completely saturated. This non-uniform delivery is the primary cause of the short lifetime of these devices as the initial saturated device typically delivers vapor in excess of that required.

Another disadvantage of these simple devices is that to extend the lifetime requires a manual procedure to refill the device or replace it, and there is no provision for being able to retrieve such a device conveniently from a remotely deployed location. In addition, although these devices can be tossed into some remote locations, they are not specifically designed for this type of deployment and therefore may not operate effectively.

There are also delivery methods for providing an air modifying agent that are energized devices, i.e. they rely on stored energy, such as a battery, or require electrical power. Requiring electrical power from a household outlet necessarily limits the ability to locate the device in hard to reach locations. Likewise, a battery operated device suffers from the disadvantages of either (1) the size or mass required for conventional sized batteries, or (2) the expense and short lifetime of typical button-sized batteries. Additionally, the difficulty of changing a battery is complicated in the application of the device in difficult to reach locations.

The most familiar example of a vapor delivery device is a common air-freshener, where an aromatic substance, in liquid form, is contained in a vented container. The method of delivery of an air-modifying agent includes an integrated liquid reservoir connected to an evaporative surface. The liquid is then internally transported to an evaporative surface from which the air-modifying vapor emanates. These devices generally contain a reservoir of the desired vapor in liquid form, an evaporative surface from which the liquid solution evaporates and a delivery mechanism which transports the liquid continually from the reservoir to the evaporative surface. These types of reservoir containing evaporative sources are well known as air-modifying devices and are commonly used as "air fresheners" or "insect repelling devices". During operation, the liquid air modifying ingredient is continually transported to the evaporative surface, typically through wicking or capillary action, without the application of external power. From the evaporative surface, the desired liquid solution evaporates into the surrounding air flow through apertures or vents. The air modifying ingredient then evaporates into the surrounding air until the reservoir is depleted.

This integrated reservoir method is typically able to achieve a more constant delivery rate of the desired vapor and thus increase the lifetime of the device. The primary disadvantage of the integrated-reservoir air freshener, as described in the prior art, can be appreciated once one considers remotely deploying such a device by tossing or rolling. The existing devices were never intended, nor designed, to be tossed, rolled or thrown. Particularly, these devices do not contain any combination of design features required to accomplish remote deployment.

SUMMARY

In the case of discouraging rodents or pests, it is often desirable to modify the air in a particular location that is not easily accessible, such as behind or underneath a cabinet or inside the construction of a wall. It is often the case that in these difficult to reach locations, small gaps in construction can function as entry points for rodents or vermin. The locations often have restricted airflow and contain a relatively small volume of air about the entry point location. If an entry point in a constricted area such as this is suffused with the appropriate concentration of a rodent or vermin, repelling vapor, it can create a barrier to rodents or pests, blocking their entry In order to accomplish this function in a convenient and effective manner, it is advantageous to have a device that; can be deployed by tossing or rolling; is relatively compact in size; automatically assumes a desirable orientation after deployment; begins or continues operation in a hands-free manner after deployment; and operates effectively for the longest possible period of time.

In order to toss or roll a vapor producing device into a hard to reach location, it is desirable that the device have an approximately spherical shape to its outer structure. It is also important that the device is constructed of materials of suitable durability so that components of the device do not fracture or break with the impacts of deployment. Additionally, if the device has multiple parts, they must be attached securely to each other so that the device stays together and functions properly after deployment.

Vapor delivery devices also typically require the storage of some amount of the vapor producing substance or substances somewhere in the interior of the device. It can also be appreciated that for the rodent or vermin repelling application, the geometry of the space or access to the space where the device is to be deployed may be narrow or physically limiting. It is thus desirable that the device is relatively compact. However,since the operating lifetime of the device is dependent on the amount of stored vapor producing substance, it is important that this storage volume is maximized. It can be appreciated that an approximately spherical shape also serves to provide the largest interior volume for a given maximum device dimension. Thus the approximately spherical shape is desirable not only for tossing and rolling during deployment, but to maximize internal storage volume and therefore maximize the device operating lifetime.

Additionally, if the device is deployed in a difficult to reach location, it will likely not be convenient to manipulate or handle the device, such as to activate it, or to start it operating after it is deployed. This ability to have the device begin operating effectively after deployment without contact or manipulation would typically be described as "self-starting" or "hands-free" activation. There are three convenient methods for providing hands-free operation in regard to activating the device after deployment. The first hands free approach would be some technique for remotely starting the device, initiated perhaps by sound or radio communication. The second hands-free starting approach would be to design a device with some type of self-starting mechanism. This might involve some type of timing mechanism, or a mechanism initiated by the impact of deployment for example. The third method of hands-free activation would be a device that could be primed, or started prior to deployment, that is then able to operate continuously throughout and after deployment. It can be appreciated that in the typical application of a remotely deployable vapor delivery device, some type of self-starting or hands-free activation is required after deployment.

It is also desirable that a remotely deployable vapor delivery device achieve a final orientation that allows it to operate effectively. It is common for standard vapor delivery devices to require a particular upright position in order to operate most effectively, or in some cases, to operate at all. In the case of a remotely deployable vapor delivery device, if the designed device requires a particular orientation to be most effective, then it should be self-righting, i.e. automatically orienting itself to the desired orientation after deployment. Automatic orientation of the device, or equivalently a "self-righting" feature, implies that the device achieves a desirable or effective operating position by itself after deployment, in a hands-free manner, without contact or manual intervention.

Furthermore, it would be desirable for remotely deployable vapor delivery device to operate for a significant amount of time. For example, if one is interested in keeping rodents or pests out of a cabinet, typically one would like to do so for as long as possible, ideally for weeks or months as opposed to only a few days or less. The lifetime of the device is typically determined by the total supply of the vapor producing substance stored within it, as well as the vapor delivery, or usage rate. It is desirable then that the device makes the most efficient use of the stored vapor producing substance. Given that there is typically a desirable vapor delivery rate to be effective for a given application, it would be desirable to maintain an approximately constant vapor delivery rate at that level. A higher vapor delivery rate would typically not be more effective, and would waste the limited supply of stored vapor producing substance, shortening the lifetime of the device. A vapor delivery rate less than the effective rate would obviously imply that the device is not functioning in a desirable manner and is not being effective. Thus, in addition to maximizing the stored volume of vapor producing substance, it is also highly desirable in a remotely deployable vapor delivery device, to maintain the vapor delivery rate at an approximately constant, effective level. Achieving both of these features would give the device the longest effective operating lifetime for a given device size.

A separate feature that is desirable in a remotely deployable vapor delivery device is that it is non-energized, requiring no stored or external power, A non-energized device is more convenient for remote deployment since it would be difficult to plug in a device once deployed in a hard to reach location, as well as difficult to deploy a device with an attached power cord. On board storage of power, such as the use of batteries, would include three disadvantages. One disadvantage would be the possibility that the device becomes ineffective when the batteries run out, the second is that this would require the inconvenience and expense of changing the batteries, and the third disadvantage is that the batteries and associated circuitry would consume device volume that could otherwise be used for additional storage of the vapor producing substance, effectively shortening the operating lifetime of such a device.

An additional feature that is desirable in a remotely deployable vapor delivery device is that it is tamper resistant. Particularly with the application of repelling rodents or pests, it is desirable to prevent them from disassembling or dismantling any part of the device and rendering it nonfunctional. It is also desirable to keep pets and small children from possibly taking the device apart, making it inoperable or possibly harming themselves with its components. For remotely deployable devices, it would be expected that the location of the deployed device would typically make it inaccessible already.

Another desirable feature for a remotely deployable vapor delivery device is that it is easily retrievable. At some point the device will exceed its useful operating lifetime and at such a time it would be desirable to retrieve the device to refill or replace it. In the case of remote deployment, it may be difficult for a person to easily reach the device with their hands. In this application it would be desirable to design the device in such a way that it could easily and conveniently be retrieved with a retrieval apparatus, such as a thin rod, stick, wire or string.

To summarize regarding the desirable features of a remotely deployable vapor delivery device, it is desirable to have a device with features that include a relatively compact size, an approximately spherical outer geometry, robust materials and attachments, continuous hands-free, remote or self-starting operation once deployed, self-righting to a desirable operating position, an approximately constant vapor delivery rate, maximized storage volume of the vapor producing substance, the longest possible operating lifetime, non-energized operation, tamper resistance and the ability to be easily retrieved.

One example of the application of a remotely deployable vapor delivery device is to the repelling of rodents or other vermin from known entry points to a particular area such a house, garage, shed, workplace or any other desired area. This approach differs from other strategies such as constructing barriers that block access, setting traps, or setting out poisonous bait. The use of repelling vapors is a method in which the goat is not to trap or kill the vermin, but simply to keep them away. In this sense, this particular application of a remotely deployable vapor delivery device is an "animal friendly" approach. It also has the advantage that the user does not need to deal with any live, dead or injured animals in the process of keeping them out of the desired area.

For rodent repelling applications, due to the typical presence of people or pets in the general vicinity of deployment, it is advantageous if the repelling vapors would be comprised of natural, nontoxic substances. Ideally such a repelling vapor would be noxious and offensive to vermin, but not pose a hazard to humans, pets or the environment. It would also be desirable if the odor of the repelling vapor used were pleasing to people.

In the first embodiment, the device presented in this application comprises an approximately spherical ball with a vented top-half and a solid hollow bottom half. In the first embodiment, the hollow bottom half includes the interior portion which contains the desired vapor producing substance. The hollow hemispherical bottom half, in combination with an interior lid, forms an integrated reservoir that contains the vapor producing substance, typically a liquid or oil from which the desired vapor will be produced. Additionally, in the first embodiment, a wick is placed inside the hollow reservoir and protrudes through a small hole in the lid of the integrated reservoir and into the vented hemispherical top half, forming an evaporative surface from which the vapor emanates. The vapor is then in contact with the surrounding air due to the vented hemispherical top half of the device. Due to the relatively constant surface area of the wick, the vapor evaporates from it at an approximately constant rate. In this first embodiment, capillary action will continually draw fluid from the reservoir to the exposed evaporative surface until the reservoir is depleted. The device of the first embodiment can be primed through a simple action such as inverting it and letting gravity drive the liquid to the exposed portion of the wick which forms the evaporative surface. Once primed, the device will operate continually and hands-free, not requiring any contact, manipulation, stored power or external power. In the first embodiment, the device includes a weight distribution with the center-of-mass in the hemispherical bottom half of the approximately spherical structure, which in turn causes the device to be "self-righting" when deployed. A vertical orientation allows the device to operate efficiently and with the longest operating lifetime, because the vapor delivery is controlled by the capillary action of the wick. In the first embodiment, the vented hemispherical top half also provides for tamper resistance, because it encloses the evaporative surface. In the first embodiment, a pin and slot design requires a twisting motion to attach the upper and lower halves of the device, which provides additional tamper resistance.

The second embodiment of the device presented in this application includes a small flat surface at the lowermost portion of the bottom half to aid in the self-righting capability of the device. The small flat surface will provide a natural tendency for the device to stop rolling or rocking once it is close the optimal vertical orientation. The small flat surface also provides some resistance to changes in orientation that might occur if the device is disturbed after deployment. The second embodiment also includes a small magnetic portion so that the device can be easily retrieved with a simple retrieval device such as a second magnet on the end of a pole or string.

This patent application describes a vapor delivery device which combines necessary and desirable features to be conveniently and effectively deployed in a difficult or hard to reach location. A first advantage of the first embodiment of the device in this application is that it includes an approximately spherical shape, which makes the device conveniently tossed or rolled and also allows the volume of stored vapor producing substance to be maximize second advantage of this first embodiment is that it can be fabricated in a relatively compact size. The third advantage of the first embodiment of the device described in this application is that it includes a means for maintaining an approximately constant vapor delivery rate. This provides for the longest possible operating lifetime by efficiently using the limited volume of stored vapor producing substance. The fourth advantage of the first embodiment is that it includes a hands-free activation capability. The fifth advantage of the first embodiment includes a weight distribution that makes the device self-righting after deployment. The sixth advantage of the first embodiment includes that it is tamper resistant. The seventh advantage of the first embodiment is that it is non-energized. The eighth advantage of the first embodiment includes that it features a modest number of low cost parts that are readily manufactured and assembled. A second embodiment is described in this application which includes additional features and advantages. The first advantage of the second embodiment includes a self-righting ability that is further enhanced. A second advantage of the second embodiment includes a feature that makes the device easily retrieved.

These advantages give the embodiments of the remotely deployable vapor delivery device described in this application a utility that does not exist in previous art. The remotely deployable vapor delivery device described here is a superior device in that it is able to modify the air in a hard to reach locations in a convenient, effective and cost effective manner. These and other advantages of one or more aspects of the of the device presented in this application will become apparent from a consideration of the ensuing description and accompanying drawings.

DESCRIPTION OF THE DRAWINGS

FIG. 1 shows a perspective view of a first embodiment of a completely assembled device.

FIG. 2 shows an exploded view of the device of FIG. 1.

DETAILED DESCRIPTION OF THE INVENTION

Figure 1:
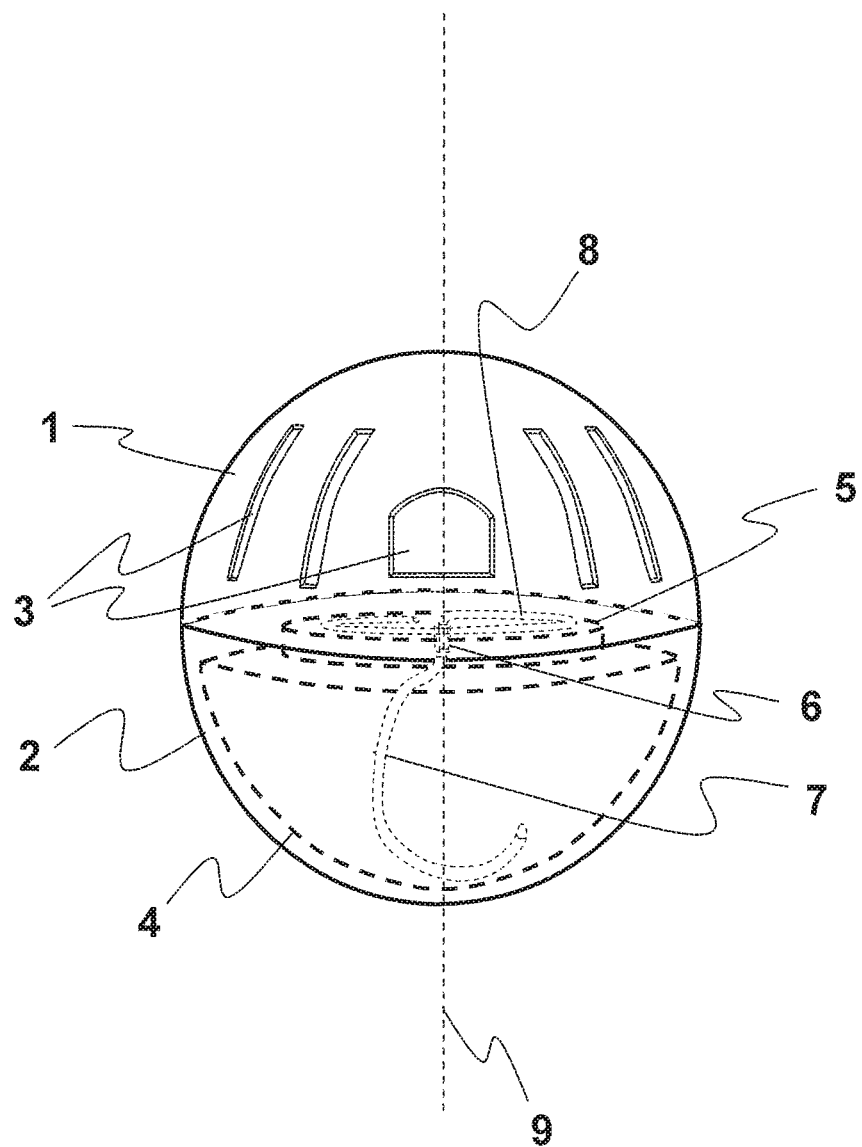
Figure 3:
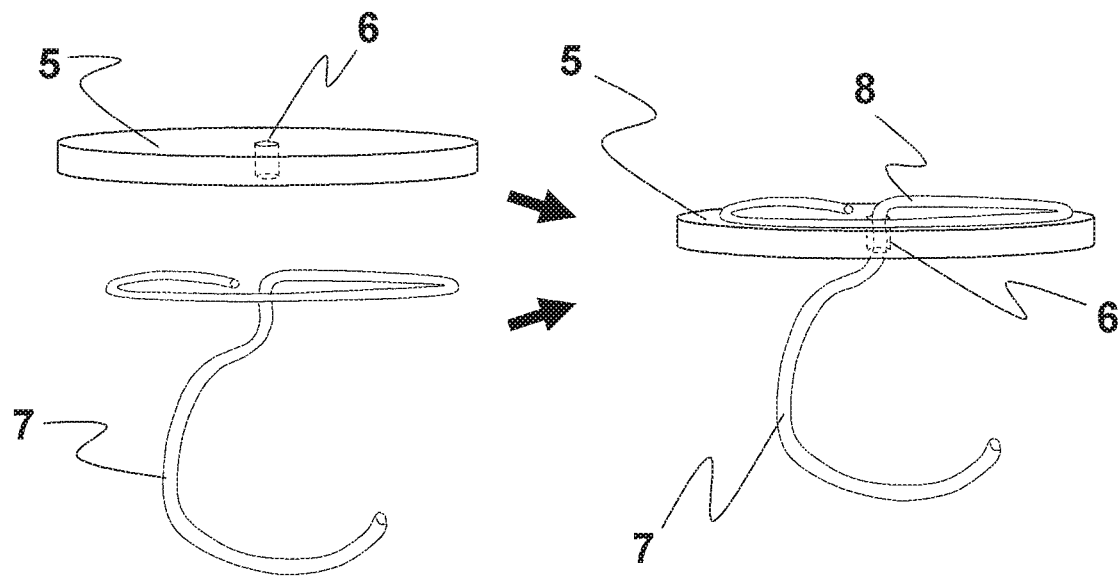
FIG. 3 shows the details of interior components of a device described herein.

In the first embodiment as shown in FIG. 1, the remotely deployable vapor delivery device consists of a vented hemispherical top half (1) attached to a hollow hemispherical bottom half (2). In combination, when the two halves of the device are attached together, they form an approximately spherical structure. The preferred diameter of the attached, approximately spherical structure is 1.875", in order to fit into spaces less then 2" in extent. The vented hemispherical top half (1) contains numerous vent holes (3) so that air can flow freely through it. In this manner the airflow of the vented hemispherical top half (1) is able to mix, by drift and diffusion, with the air in the environment surrounding the device. The hemispherical bottom half (2) is attached to a reservoir lid (5) forming an integrated reservoir (4), which is the portion of the device that contains the vapor producing substance. The interior components of the device, as detailed in FIG. 3, consist of a reservoir lid (5) with a thru-hole (6) and a wick (7).

When assembled, the wick (7) is in contact with the liquid in the integrated reservoir (4) and extends thru the thru-hole (6) in the reservoir lid (5) and into the upper half of the device, where the outer surface of the wick forms an evaporative surface (8). In the first embodiment, the reservoir lid (5) is attached to the upper surface of the hemispherical bottom half (2) using an adhesive material that is not shown. The thru-hole (6) is of a diameter slightly smaller than the diameter of the wick (7), in order that the thru-hole (6) squeezes the wick (7) slightly to form a tight enough seal that minimizes evaporation of the vapor producing substance directly from the reservoir (4) to the surrounding air. In the first embodiment, the fibrous wick (7) is 0.125" in diameter and the thru hole (6) is 0.09375" in diameter. The optimal operating position is when the device of the first embodiment is positioned such that the central axis of the device (9) is oriented and aligned with a vertical direction.

Figure 2:
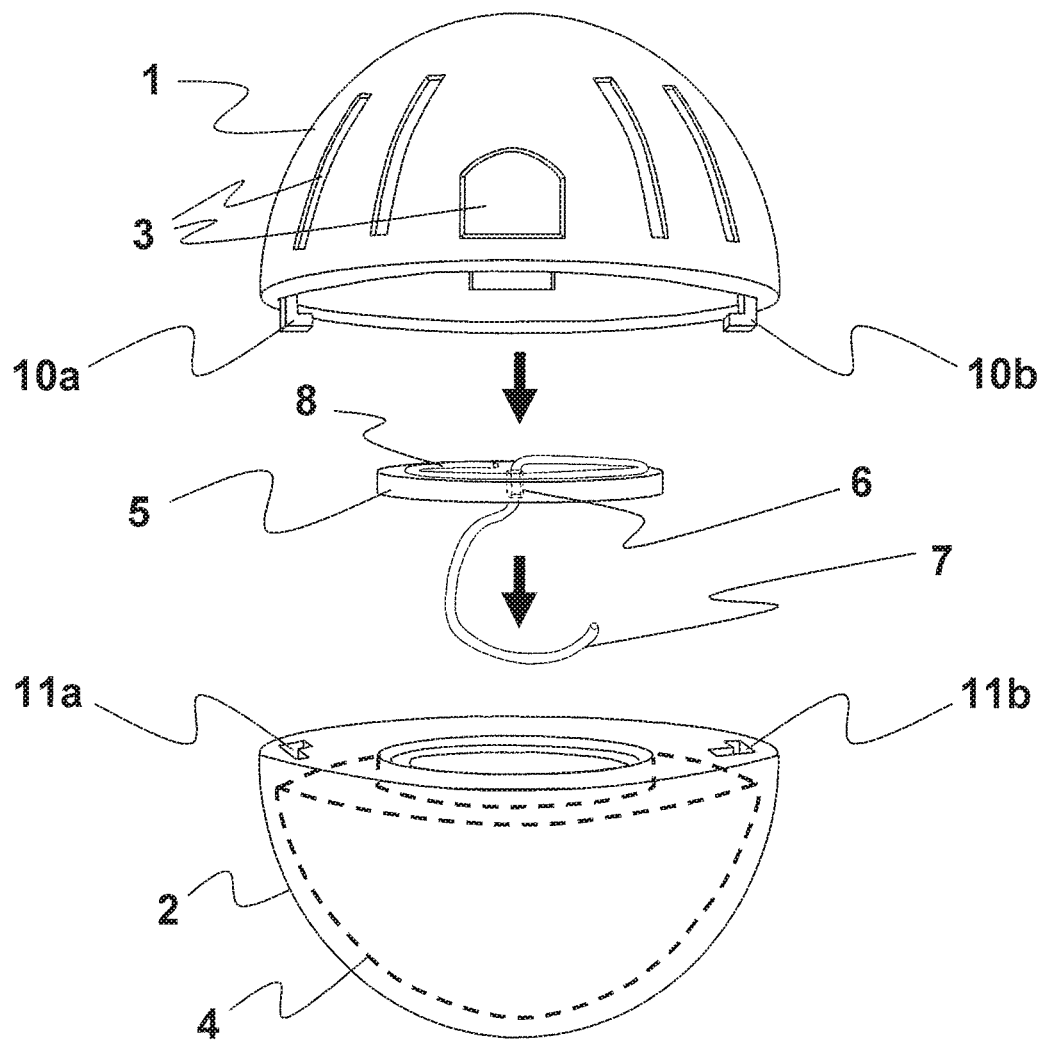
Figure 4:
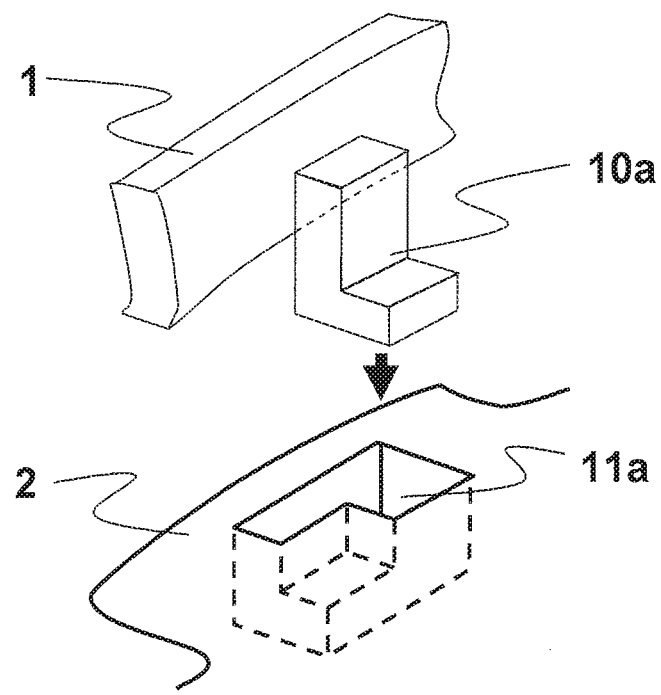
FIG. 4 shows the details of an example of a fastening mechanism for the two halves of the device in a first embodiment.

In the first embodiment, the two halves of the device are constructed separately, as can be seen most clearly in FIG. 2. In FIG. 2 it can be seen that the vented hemispherical top half (1) includes protruding pin structures (10a and 10b) that fit into a matching recessed slot structures (11a and 11b) in the flat upper portion of the hemispherical bottom half (2), allowing the two halves to be securely assembled by inserting the protruding pin structures (10a and 10b) into the recessed slot structures (11a and 11b) and twisting slightly. For clarity, a detailed view of one of the first embodiment protruding pins (10a) and one of the first embodiment recessed slot structures (11a) are shown in FIG. 4.

During operation of the first and second embodiments of the device, the wick (7) absorbs the vapor producing substance or fluid in the integrated reservoir (4), whereupon it is transported by capillary action up the wick (7), thru the thru-hole (6) in the reservoir lid (4) and reaches the evaporative surface (8). The desired air-modifying vapor is then formed by evaporation of the vapor producing substance from the evaporative surface (8). The desired vapor is then able to drift and/or diffuse through the vent holes (3) and thereby mix with the air in the environment surrounding the device. The vapor will continue to be delivered in this manner to the air surrounding the device until the vapor producing substance in the integrated reservoir (4) is depleted. The capillary action is driven by the continual evaporation of the fluid from the evaporative surface (8) along with surface tension forces of the fluid contained within the wick, which pulls the fluid along the wick, up from the reservoir (4) to the evaporative surface (8). In one non-limiting application of the device, the liquid contained in the reservoir (4) is 100% peppermint oil and the vapor produced is used to repel rodents such as mice or rats.

It can be appreciated that the device, as described in this first embodiment, would need to be primed at the start in order for the vapor delivery to be initiated. That is to say, that the wick (7) and the evaporative surface (8) must be damp with fluid at the start of operation. This can be readily accomplished at the start by filling the reservoir and assembling the reservoir lid and attaching the two hemispherical halves of the device, and then manually tipping the device upside down (causing the hemispherical bottom half (2) to be above the vented hemispherical top half (1)). In this position, gravity will cause the fluid in the reservoir (4) to be transported downward along the wick (7), eventually saturating the evaporative surface (8). With the exposed portion of the wick (7) thus saturated, the device can then be returned to the upright position with the top half (1) above the hemispherical bottom half (2). At this point the device is then primed and will begin to deliver the desired vapor to the surrounding air. The device will then operate continuously and can then be deployed by placing it upright or remotely deployed by rolling or tossing it into position, such as behind cabinets, within walk or in other hard to reach locations. Once primed in this manner and deployed, the device will continue to operate after deployment, with the fluid being continually drawn from the reservoir by capillary action, until the vapor producing substance in the reservoir (4) is depleted. It is important to note that this type of operation is non-energized and completely hands-free; requiring no manual intervention once the device is deployed.

Removing the reservoir lid (5) allows access to the hollow integrated reservoir (4) for the initial loading of the vapor producing substance, for example, 100% peppermint oil. Once the reservoir lid (5) is installed, it functions to seal the integrated reservoir (4), except for the protruding wick (7) extending thru the thru hole (6). The wick (7) contacts the liquid solution in the integrated reservoir (4) and also forms the evaporative surface (8) that contacts the exposed air inside the vented hemispherical top half (1) of the device. The wick (7) should contact the entire depth of the integrated reservoir (4) in order that all of the vapor producing substance will eventually be drawn thru the wick (7) over the lifetime of the device. The wick (7) should also contact a substantial portion of the volume of the integrated reservoir (4) in order to further ensure that all of the solution will contact a portion of the wick (7), even if the device is not deployed in a perfectly vertical position. This ensures that the device will still operate successfully, even in the event that when it is deployed, it is somehow blocked from attaining a perfectly vertical position.

It can be appreciated to those skilled in the art, that the capillary action fluid delivery mechanism described herein would give an approximately constant vapor delivery rate, with the vapor delivery rate being driven primarily by the evaporation rate of the fluid from the evaporative surface (8). The evaporation rate would be determined predominantly by the vapor pressure of the desired fluid, the surface area of the evaporative surface (8) and the ambient temperature. For a given air-modifying fluid and temperature, the length of the exposed portion of the wick (7) forming the evaporative surface (8) can be adjusted to give the desired vapor delivery rate as required for the desired effect. In the first embodiment, the exposed portion of the wick (7) forming the evaporative surface is 0.125" in diameter and 3" in length. This exposed portion lies on top of the reservoir lid (5) in the vented hemispherical top half (1) of the device as shown in FIG. 1 and FIG. 2. By setting the constant vapor delivery rate to just the amount required for effectiveness in the desired application, the operational lifetime of the device can be maximized. Optionally, the user can set the delivery rate to slightly higher than required, by increasing the length of the exposed portion of the wick (7) so that the device will remain effective even with minor temperature variations.

In the first embodiment, the device is also naturally self-righting and will seek the optimal vertical position when tossed or roiled. The numerous vent holes (3) of the vented hemispherical top half (1), as compared to the solid-walled, liquid containing integrated reservoir (4) of the hemispherical bottom half (2) causes the center of mass of the assembled device to be contained within the volume of the of the bottom hemispherical bottom half (2). The low center of mass of the approximately spherical device causes gives an inherent self-righting feature to the operation of the device. In other words, when tossed or rolled, and when unobstructed, the device will naturally settle into an upright position with the vented hemispherical top half (1) above the hemispherical bottom half (2) without manual intervention, as depicted in FIG. 1. This is due simply to the fact that an unobstructed spherical object, with a weight distribution such that its center-of-mass that is not at its geometrical center, will tend to reduce gravitational potential energy by settling into a position with its center-of-mass at the lowest position possible. In the case of the first embodiment, this means that the device will tend to settle with the more massive, fluid containing hemispherical bottom half (2) on the bottom, and the vented hemispherical top half (1) on top. Additionally, the larger mass of the solid walls of the hemispherical bottom half (2) of the device, as opposed to the lighter mass of the vented hemispherical top half (1), ensures that even as the vapor producing substance in the integrate reservoir (4) becomes depleted, the center of mass of the device will remain in the hemispherical bottom half of the assembled device and it will tend to remain upright, even if disturbed.

This vertical position is the optimal position for the long term operation of the device, ensuring that the fluid transport from the reservoir (4) to the evaporative surface (8) is controlled by capillary action. An ideal vertical position to provide a maximum operational lifetime would be with the vertical axis (9) of the approximately spherical device of FIG. 1 to be exactly vertically aligned. This is not critical however and nearly ideal operation would be achieved with the vertical axis (9) aligned within 30° of vertical. In the case of a deployed device that is obstructed and does not attain an ideal upright position, with a portion of the integrated reservoir (4) above a portion of the evaporative surface (8), then the there would be a tendency for the fluid delivery to be enhanced by gravitationally driven flow. In this non-ideal case, the fluid in the reservoir would have a tendency to be depleted slightly more rapidly, somewhat shortening the operational lifetime of the device. It can be appreciated then, that the self-righting nature of the device, in this first embodiment, is a key feature to its optimal operation and in particular to achieving a long operating lifetime. It can also be appreciated that even in a non-optimal position; the device would still operate successfully, simply for a shorter period of time, determined by the actual deployed orientation.

It can also be appreciated that the construction of the device, with a vented hemispherical top half (1) can be designed optimally to protect the evaporative surface (8) portion of the wick (7) from tampering by vermin, pets or people. This tamper resistant design is accomplished through the protective nature of the vented hemispherical top half (1) of the device with its small but numerous vent holes (3). In the first embodiment, the vent holes (3) of the vented hemispherical top half (1) are approximately 0.125" in diameter, with a center to center spacing of 0.1875". It can be appreciated that a range of sizes and shaped can be used for the vent holes, with the desired features being that the air can flow freely through the vented hemispherical top half (1) of the device while access through the vent holes (3) for typical toes, teeth and fingers of typical vermin, pets or people is prevented.

It is possible that the user of this remotely deployable vapor delivery device might desire to change the vapor delivery rate when deployed. For example, this might be the case if there is a sizable temperature difference to be expected after deployment. Another example might be an unusually small volume of area of deployment. For application in higher temperatures, it would be desirable to increase the length of the evaporative surface (8), to maintain the optimal vapor delivery rate, and for lower temperatures, to shorten the length of the evaporative surface (8).

During operation, the remotely deployable vapor delivery device will typically be tossed or rolled. In order to be tossed or rolled, the vented hemispherical top half (1), hemispherical bottom half (2), and all the parts and attachments contained therein must be of suitable durability to withstand the stresses, strains and shocks which will occur upon the impacts due to tossing and rolling or a combination thereof. The strength and durability is determined by the material of which these components are constructed, as well as the geometry, including the radius of the vented hemispherical top half (1) and hemispherical bottom half (2), the thickness of the structural material which forms the vented hemispherical top half (1) and hemispherical bottom half (2) as well as the size and number of the vent holes (3). In the first embodiment, in order to accomplish the required strength and durability, the vented, hemispherical top half (1) is constructed of a durable material such as polypropylene. In the first embodiment the radius of the hemispherical portion of the vented hemispherical top half (1) is approximately 0.9375", the vent holes (3) are approximately 0.125" in diameter and have at least a 0.1875" center to center spacing. In the first embodiment, the thickness of the structural material that forms the hemispherical portion of the vented hemispherical top half (1) is approximately 0.0625". Additionally, the fastening mechanism comprised of the protruding pins (10a and 10b) and matching recessed slots (11a and 11b) must be of sufficient strength and holding power to withstand the stresses, strains and shocks that occur during the process of deploying the device.

In the first embodiment, the bottom half (2) contains an integrated reservoir (4) which is sealed with a reservoir lid (5) through which a wick (7) extends thru a thru-hole (6), such that it contacts both the contents of the reservoir as well as the airflow in the upper half (2) of the device. In the first embodiment, the hemispherical bottom half (2) matches the vented hemispherical top half (1) and is also 0.9375" in diameter, in order to form an overall approximately spherical structure when assembled. In the first embodiment, the hemispherical bottom half (2) with integrated reservoir (4) and reservoir lid (5) are also constructed of a durable material such as polypropylene, and constructed of 0.0625" thickness.

In the first embodiment the reservoir lid (5) contains a 0.09375" hole (6) through which is penetrated by the wick (7) of approximately 0.125" diameter and 6" in total length. The evaporative surface (8) is formed by portion of the wick (7) that is protruding from the thru-hole (6) and this protruding portion is preferably 3" in length. The remainder of the wick (7) is in contact with the vapor producing substance inside the integrated reservoir (4) and this portion is preferably 3" in length. The length of the wick (7) is intentionally longer than that required to reach the bottom of the integrated reservoir (4) in order to allow for any desired adjustments in the length of that portion of the wick (7) that forms the evaporative surface (8). The wick (7) of the first embodiment is comprised of a fibrous, wicking material such as ordinary cotton string, available at any typical craft store, hardware store or drugstore.

A key feature to the optimal performance of a remotely deployed vapor delivery device is that it is able to operate for the maximum possible lifetime. The longest operational lifetime is attained by maximizing the volume of the integrated reservoir (4). However, this must be balanced with the requirement that the overall size of the device be kept relatively small, in order for it to be deployed in hard to reach locations which are often constricted in size in at least one dimension. Typical locations behind cabinets or within walls may only have a clearance of 2" or less. For a given minimum clearance, the geometry for a deployable device with the largest possible volume is a spherical shape with a diameter slightly smaller than the minimum clearance. The first embodiment has an outside diameter of 1.875".

Figure 5:
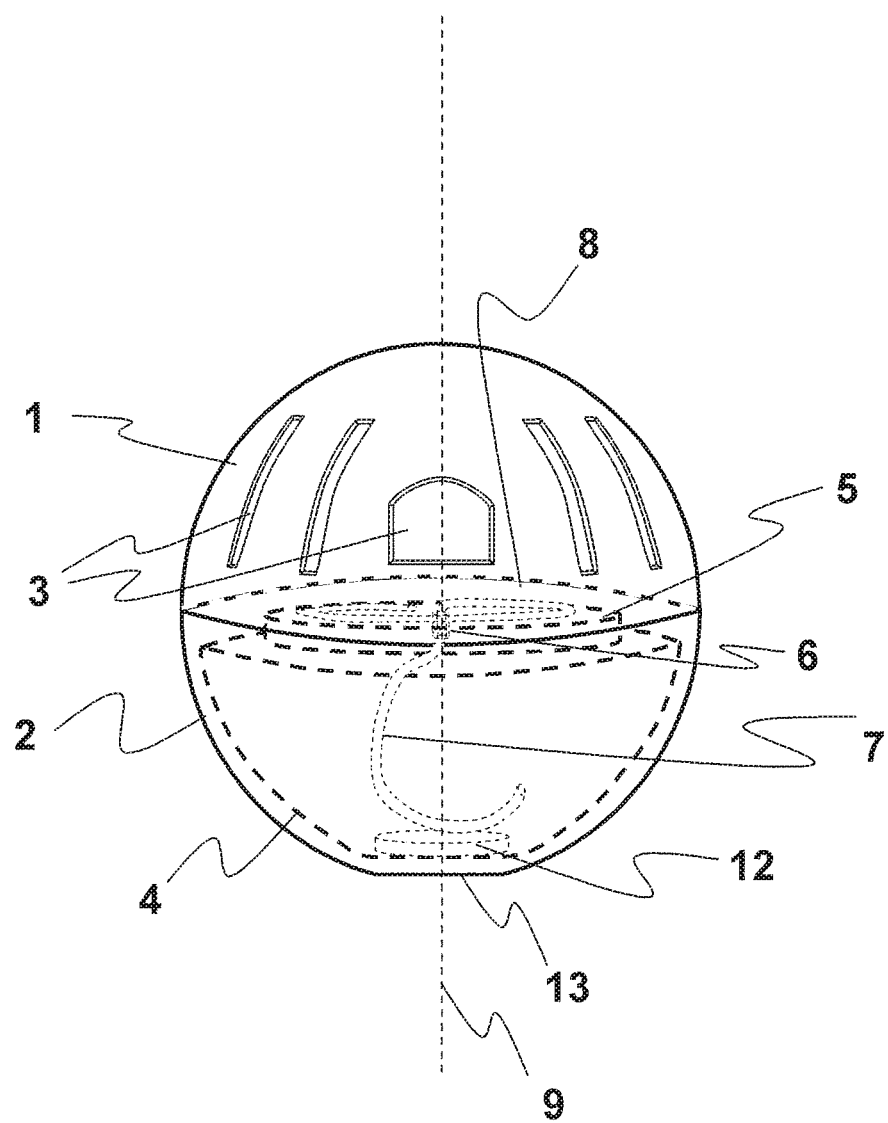
FIG. 5 shows a perspective view of a second embodiment of the completely assembled device.
Figure 6:
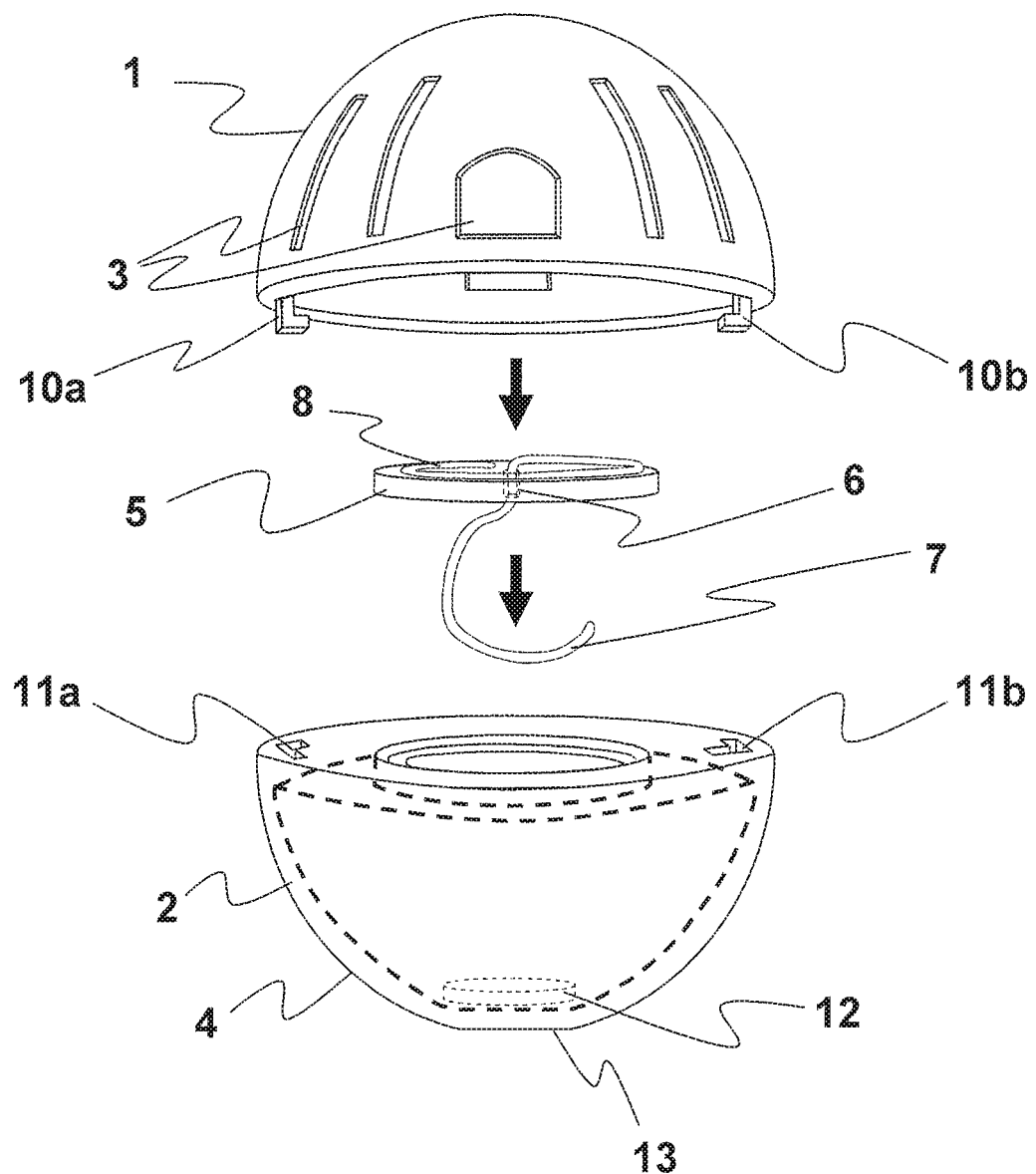
FIG. 6 shows and exploded view of the device of FIG. 5.

The theoretical maximum hemispherical volume of a 1.875" diameter hemispherical bottom half (2), not including wall thicknesses, would be 23 milliliters. Accounting for the volume of the wall and lid of the integrated reservoir (4), assuming a 0.0625" wall and lid thickness would result in a usable volume of approximately 20 ml. A prototype device with a 15 ml reservoir and a 6" long wick with 3" exposed as an evaporative surface (8), maintained a dampened wick for approximately 4 months at room temperature. Therefore, it is expected that the device as described in the first embodiment, with a 20 ml reservoir, and a 6" wick with a 3" exposed length forming the evaporative surface should last proportionately longer, or 4 to 6 months, depending on the ambient temperature A drawing of a second embodiment of the remotely deployable vapor delivery device is shown in FIG. 5 and FIG. 6. FIG. 5 shows an assembled view of the second embodiment and FIG. 6 shows an exploded view of the second embodiment. In addition to the features and components of the first embodiment, this second embodiment includes the additional feature of a magnetic mass (12) attached to the interior of the hemispherical bottom half (2). The second embodiment also includes the additional feature of a small flat surface (13) at the lowermost portion of the hemispherical bottom half (2).

In the second embodiment, the ability to remotely deploy this device is further enhanced by attaching a magnetic mass (12). The magnetic mass (12) can be attached to the device by any convenient method, for example by adhesive or mechanical fastening. The magnetic mass (12) makes the device easy to retrieve from a hard to reach location with a simple retrieval device such as a second magnet on the end of a rod or string. The size and mass of the magnetic mass (12) should be designed such that its weight does not substantially reduce the ability to roll the device during deployment, but also large enough that sufficient magnetic force is generated to retrieve the device with a second magnet. In the first embodiment, a ¼" diameter cobalt magnet is used as the magnetic mass (12). A ferrous or other magnetic metal may also be used as the magnets mass.

Convenient retrieval is highly desirable in a device that can be deployed by tossing or throwing because in some cases, the access path to the location where the device is deployed may be smaller than a typical person's hand or wrist, and/or further than the length of a typical person's arm. It is also highly desirable to be able to retrieve the device in the event that the initial deployment does not reach the desired location, such as might be described by a "bad" toss or throw. In this case, the user would like to be able to retrieve the device so that they can deploy it again. It can also be appreciated that for a disabled person or persons, the ability to magnetically attach the device magnetically to the end of a long pole or string would be invaluable not only for retrieval, but also for the initial deployment of the device as well.

The self-righting tendency of the device is further enhanced in the second embodiment by making a small flat surface (13) at the lowest point of the hemispherical bottom half (2) of the device. This would increase the tendency of the device to settle into a precisely upright position, as well as allowing the device to be conveniently set in a perfectly upright position by the user, if desired. This small flat surface (13) must be made relatively small in diameter, such that it does not interfere or prevent the device from rolling freely at the typically higher speeds the device will experience when it is initially deployed. In the second embodiment, a flat spot of ³⁄₁₆" diameter is formed in the outer surface of the hemispherical bottom half (2) of the device.

The first embodiment is constructed with an overall diameter of approximately 1.875". It is apparent that the same device can be constructed with a range of diameters. The overall diameter affects the available storage volume of the integrated reservoir (4) and hence the overall operating lifetime of the device. The overall diameter also affects the access opening size required to deploy the device in remote locations. The smaller the overall diameter of the device, the easier it is to deploy through smaller and smaller access openings It is apparent that the device could be constructed in a range of sizes. The device could be fabricated to microscopically small sizes, provided suitable manufacturing techniques and materials are used. The device could also be fabricated to many inches in diameter, for example, up to 18" in diameter. A larger size device would be suitable for larger vapor delivery applications, including deterring larger animals.

In terms of material construction of the device, the vented hemispherical top half (1) and the hemispherical bottom half (2) can be fabricated from different materials than described in the first embodiment, including different types of polymers, plastic, composites, ceramic, metal or wood. For example, the vented hemispherical top half (1) could be fabricated from a metal or plastic mesh or screen. It is also not required that various components of the device are constructed from the same materials.

It is also apparent that a variety of designs and geometries could be used for time vent holes (3) in the vented hemispherical top half (1) of the device without deviating from the scope of the present invention. For example, the device can be fabricated with the entire top half (1) consisting of vent holes (3) as in the first embodiment or it could have a lesser number of holes or only one hole. The vent holes can be of any number, shape or size, with the intention of providing a path for the air contained within the vented hemispherical top half (1) of the device, to contact, drift, mix and diffuse with the air immediately surrounding the device. It is also apparent that the vent holes (3) could be located in either or both the vented hemispherical top half (1) or bottom half (2) of the device. Adjustable vent holes (3) could also be readily incorporated, for example, by fabricating a sliding mechanism that can be adjusted to open, close or partially close the vent holes. Similarly, the vent holes (3) could be of such a suitable shape and size that they are not tamper-resistant from vermin. This could be desirable in applications where the tamper-resistant feature is not necessary or in such cases that the repelling nature of the device keeps the vermin away such that tampering is not an issue.

It can be appreciated that the wick (7) and evaporative surface (8) could be fabricated from a number of different materials, such as plastic, composites, wood or metal. Any material that can be fabricated in such a manner as to be porous or containing narrow channels therein, could be used to provide a means of a constant vapor delivery rate in combination with a continuous flow of the vapor producing substance. In addition, solid materials that do not allow fluid transport directly through them could be fabricated with nano scale, micro scale or miniature channels to allow fluid to flow through them as well. In this way, solid materials could be made to function in the manner described for vapor producing substance transport within the device. The delivery mechanism and evaporative surface could also be fabricated from different materials, such as one being made from plastic and one from cotton fiber.

Additionally, the delivery mechanism, as described here, uses a 0.125" diameter, 6" long wick (7). The wick (7) functions as both the delivery mechanism and also the exposed 3" portion serves as the evaporative surface (8). It is apparent that the dimensions of the wick (7) could be varied over a range of lengths and diameters. In non-limiting typical applications, the wick (7) could vary from 0.015" in diameter to 0.25" in diameter. Also in non-limiting typical applications, the wick (7) could vary from 0.25" in length to 18" in length. Additionally, the exposed portion of the wick (7), forming the evaporative surface, could consist of any fraction of its length. Should the evaporative surface (8) and wick (7) be fabricated from different materials, there relative sizes can be varied as required to give a suitable vapor delivery rate.

Preferably, the fluid delivery mechanism is not energized, meaning that it does not require an integrated power source, such as a battery or an external source of power. However, an energized fluid delivery mechanism, such as a pump or other means, could be implemented as an alternative embodiment. For maximal operating lifetime of the device, the energized fluid delivery mechanism would be constructed in order to provide an approximately constant delivery rate such that all of the fluid in the reservoir is depleted before the battery, or other energy source required to power the fluid delivery, is also depleted. Alternatively, an energized fluid delivery mechanism could also be used to optimize the fluid delivery for a temporary period of time, in order to optimize the lifetime and or effectiveness of the device. Such a design for example, might include a mechanism that temporarily increases the fluid flow and hence vapor delivery rate when an integrated sensing mechanism detects motion, sound or the presence or rodents.

Other alternative embodiments include different materials and designs for the evaporative surface (8). The evaporative surface (8) of this invention can be fabricated from any material which allows the fluid delivered to it to be exposed to the airflow surrounding the device when deployed. The evaporative surface (8) could be fabricated from plastics, textile materials, composites, wood or metal. In one embodiment, a material such as a semi-permeable membrane could be used, to control the fluid delivery and evaporation process, allowing vapor to be emitted from the reservoir while preventing fluid from flowing directly through the semi-permeable membrane. In an alternative embodiment, the evaporative surface (8) can be integrated, into one of the other components of the device, such as the reservoir lid (5), the vented hemispherical top half (1) or hemispherical bottom half (2) of the device. In an alternative embodiment of the invention, the evaporative surface could be energized or enhanced to improve the effectiveness of the air-modifying nature of the device. In this alternative embodiment, the evaporation rate could be increased, for example by heating, to increase the evaporation rate as desired.

The self-righting feature is a key component of the first embodiment because it provides a mechanism for the device to attain a vertical position without manual intervention, as is the case in remote deployment. In the first embodiment, the device is designed with a center-of-mass that is contained within the volume of the bottom half (2) of an approximately spherical device, thus giving it a natural tendency to roll into an upright and vertical position as shown in FIG. 1. In addition, in the second embodiment, a small flat (13) is placed at the lowest portion of the bottom half (2) in order to enhance the tendency to settle and remain in this optimal position. The small flat (13) can apparently be designed with different dimensions, particularly as the overall size of the device is varied.

It is readily apparent that an approximately spherical shape can be achieved with a number of spherically related shapes, including but not limited to such shapes as oval, egg-shaped or elliptical. Each of these and other generally spherical shapes could accomplish the essential features of being able to toss or roll the device and have it be self-righting. Additionally, the outer surface of the device could have small facets, dimples, flats or protrusions and still be considered approximately spherical. In one alternative embodiment, the interior components of the device are freely rotating and seek an optimal vertical position independently of the approximately spherical outer shell of the device.

Another key design component of this device is the integrated reservoir (4) that maximizes the stored volume of the desired fluid for a given device size. In the first embodiment, the reservoir is integrated into the hemispherical bottom half (2) of the device, with the benefits of simplified manufacturing and also resulting in the center-of-mass of the device being within the volume of the hemispherical bottom, half (2) of the device. In an alternative embodiment, the integrated reservoir is fabricated wholly or partially in both the vented hemispherical top half (1), and hemispherical bottom half (2) of the device, providing additional volume for fluid storage. In one such embodiment, the spherically shaped bottom half (2) would be altered to actually comprise the majority of the overall spherical structure of the device and the vented hemispherical top half (1) in that case would comprise only a small portion of the overall spherical structure. In this case the integrated reservoir (4) could be formed with a larger portion of the total volume of the overall approximately spherical device. In order to still maintain the self-righting nature of the device in this embodiment, the overall center-of-mass of the device should still be in the hemispherical bottom half of the overall structure. This could be accomplished, for example, using the technique of the additional magnetic mass (12) as described in the second embodiment, and increasing the weight of the additional magnetic mass (12) in the bottom half (2) of the device, or by some other integrated self-righting mechanism.

In another alternative embodiment of this device, the integrated reservoir (4) could be comprised of a solid, porous, or semi porous material that is saturated with the desired solution. In a separate embodiment, the reservoir consists of a chamber filled with a compressed or pressurized form of the desired vapor. The key feature of the reservoir (4) is that a substantial volume of the desired solution or source material for the air-modifying vapor is stored within a confined region of the device. In the first embodiment, the reservoir is integrated into the bottom half (2) of the device, however, in alternative embodiments, the reservoir can be a separate component, attached or otherwise contained anywhere within the volume of the overall device.

A key feature of the second embodiment is that the device is easily retrieved by a convenient means such as with a magnetic material used for the additional mass (9). This allows the device to be retrieved upon the completion of its operational lifetime, when the device is improperly deployed, to adjust the device in some manner or change its location. This feature also facilitates deployment and retrieval by individuals with handicaps or disabilities. It can be appreciated that there could be a number of alternative embodiments regarding the retrieval of the device. The device can be designed to be retrieved by magnetic, electrostatic, mechanical or adhesive elements. The retrieval component of the device could be a separate material or structure attached to the structure of the device, or could also be integrated as a feature or part of one of the other components of the device. For example, the bottom half (2) could be fabricated from a magnetic material. Additionally the device could be designed such that an electrostatic attraction causes the device to be attached to the end of an oppositely charged retrieval mechanism, or an adhesive mechanism could be used to attach a retrieval mechanism to the device.

It is also possible to fabricate the device with an additional mechanical connection, comprising a thread or string that is maintained between the deployed device and the end of a retrieval mechanism, allowing the device to be retrieved. In another alternative embodiment, a thread or string is attached to the structure of the device and is held on to by the user during deployment. In this embodiment the user is still able to deploy the device by throwing it, and the device can be subsequently retrieved by pulling on the string.

Other alternative embodiments concern the method of attachment of the various components of the device, such as the attachment of the vented hemispherical top half (1) to the hemispherical bottom half (2) or the reservoir lid (5) to the bottom half (2). It can be appreciated that there are a number of methods by which two hemispherical halves (1 and 2) and reservoir lid (5) could be securely attached to each other, and it is appreciated that the protruding pins (10*a* and 10*b*) and matching recessed grooves (11*a* and 11*b*) represent but one possible option for accomplishing the attachment. For example, a plurality of protruding pin structures (10*a* and 10*b*) of alternate designs could be used in combination with a plurality of matching recessed slot structures (11*a* and 11*b*), also of alternate but matching designs. It is also possible to rearrange the locations of the protruding pin structures (10*a* and 10*b*) and recessed slot structures (11*a* and 11*b*), to be located on the different components of the device, including any combination of protruding pin structures (10*a* and 10*b*) and matching recessed slot structures (11*a* and 11*b*) on the hemispherical upper half (1) hemispherical bottom half (2) and reservoir lid (5).

The two halves could equivalently be attached any number of methods, such as the non-limiting examples of matching grooves or threads, adhesives, fasteners, chemical bonding, magnetic or electrostatic means. It is also possible that the vented hemispherical top half (1) and hemispherical bottom half (2) are designed such that they are integrated together as one component in the manufacturing process. In this case the vented hemispherical top half (1) and hemispherical bottom half (2) are already chemically bonded together as part of the manufacturing process. Similarly, the reservoir lid (5) can be attached to the top portion of the reservoir by a variety of methods, such as matching grooves or threads, adhesives, fasteners, chemical bonding, magnetic or electrostatic means. Additionally, the integrated reservoir could be designed in such a fashion that the reservoir lid (5) is already integrated with the reservoir, is of a non-circular shape, or that a reservoir lid (5) is not required.

Alternative embodiments include integrating various components and features of the device together. For example, in one embodiment, the vented hemispherical top half (1), hemispherical bottom half (2) could be integrated together. In an alternative embodiment, the vented hemispherical top half (1), hemispherical bottom half (2), reservoir lid (5), wick (7) and evaporative surface (8) could all be integrated as a single component in the manufacturing process. Additionally, the interior components of the device, the reservoir (4), wick (7), evaporative surface (8) could be integrated into a single component. In one such embodiment, the reservoir (4), wick (7) and evaporative surface (8) are integrated into a single material which has absorbed within it or otherwise contains a solid or liquid form of the desired air-modifying vapor. In this case the integrated material performs the function of the reservoir (4) wick (7) and evaporative surface (8). For example, in this embodiment, an absorbed cotton ball or gel containing the desired vapor element could be enclosed in an approximately spherical vented shell.

In one integrated embodiment of the remotely deployable vapor delivery device, the entire device is integrated into a spherical structure whose interior forms the integrated reservoir (4) and whose exterior spherical surface functions to accomplish the fluid transport and also provides the evaporative surface (8). One non-limiting example of this embodiment would be the case where the surface of the spherical structure consists of a semi-permeable membrane, or other structure fashioned such that fluid from the interior cannot escape the device, but that vapor from the interior is able to escape through the outer surface.

It is also apparent that the current device could be constructed with a plurality of integrated reservoirs (4) containing a plurality of vapor producing substances as an alternative embodiment. The device could include a plurality of means for connecting a plurality of evaporative surfaces (8) to the plurality of integrated reservoirs (4) in order to provide continuous flow of a plurality of vapor producing substances. Alternatively, the device could be constructed to use a single transport and evaporative mechanism in contact with the plurality of integrated reservoirs (4) and the plurality of evaporative surfaces (8).

From the descriptions and drawings presented in this application, the reader will see at least one embodiment of a remotely deployable vapor delivery device that can be conveniently and effectively used in hard to reach locations. The advantages of the first embodiment described in this application includes a device that can be conveniently tossed or rolled, provides a maximal amount of stored vapor producing material, is compact in size, includes a means for maintaining a continuous flow and approximately constant vapor delivery rate, provides for the longest possible operating lifetime by efficiently using the limited volume of stored vapor producing substance, includes a hands-free activation capability, includes a weight distribution that makes the device self-righting after deployment, is tamper resistant, is non-energized, and includes a modest number of low cost parts that are readily manufactured and assembled. A second embodiment is described in this application which includes the additional advantages of enhanced self-righting capability and easy retrieval.

While the above description contains specificities, these should not be construed as limitations in scope, but rather as an exemplification of the embodiments thereof. Many other variations are possible. For example, the reservoir could be sealed with a gasket or o-ring, which might require the added feature of a seat for the gasket or groove for the placement of the o-ring. Another example might be to add a small amount of adhesive material or putty to the protruding pin structures (10*a* and 10*b*) and/or recessed slot structures (11*a* and 11*b*) in order to further secure the attachment of the structural components of the device. Similarly, the device could be fabricated in a variety of different colors, out of a variety of different materials and of alternate sizes.

Thus the scope of the embodiments should be determined by the appended claims and their legal equivalents, rather than by the examples given.

Other embodiments of the present invention will be apparent to those skilled in the art from consideration of the specification. It is intended that the specification and Figures be considered as exemplary only, with a rue scope and spirit of the invention being indicated by the following claims.

What is claimed is:

1. A remotely deployable, self-righting vapor delivery device comprising:

a ball having an approximately spherical outer surface;

the ball having first and second geometric hemispheres;

a reservoir inside the ball, wherein a volume of vapor producing substance is in the reservoir and is in the first geometric hemisphere;

wherein the second geometric hemisphere has an evaporative surface positioned therein;

wherein the evaporative surface is in contact with a mechanism that transports the vapor producing substance from the reservoir to the evaporative surface;

wherein the second geometrical hemisphere comprises one or more vent holes;

wherein the center of mass, determined by the mass and distribution of all of the assembled device components and vapor producing substance is within the volume of in the first geometric hemisphere comprising the reservoir;

wherein the force of gravity will urge the device to a rest position with the first geometric hemisphere comprising the reservoir biased to a position below the vented second geometrical hemisphere.

2. A remotely deployable self-righting vapor delivery device according to claim 1 wherein the mechanism that transports the vapor producing substance to the evaporative surface comprises a wick.

3. A remotely deployable self-righting vapor delivery device according to claim 1 wherein the center of mass of all the device components of the assembled device is within the volume of the first hemisphere without any portion of vapor producing substance contained in the reservoir.

4. A remotely deployable self-righting vapor delivery device according to claim 1 which comprises a small flat portion at the lowermost portion of the outer surface of the first hemisphere that comprises the reservoir.

5. A remotely deployable self-righting vapor delivery device according to claim 1 in which the reservoir is partially in both the first and second geometrical hemispheres.

6. A remotely deployable self-righting vapor delivery device according to claim 1 in which the first hemisphere comprises a plurality of reservoirs.

7. A remotely deployable self-righting vapor delivery device according to claim 6 in which the second hemisphere comprises a plurality of evaporative surfaces.

8. A remotely deployable self-righting vapor delivery device according to claim 1 in which the device comprises a plurality of reservoirs, evaporative surfaces and/or vent holes.

9. A remotely deployable self-righting vapor delivery device according to claim 1, further comprising a magnetic retrieval mechanism.

* * * * *